US005681754A

United States Patent [19]
Pope et al.

[11] Patent Number: 5,681,754
[45] Date of Patent: Oct. 28, 1997

[54] METHOD FOR IMPROVING THE PERFORMANCE OF AN IMMUNOREAGENT IN AN IMMUNOASSAY

[75] Inventors: Mark R. Pope, Grayslake; Peter J. Tarcha, Lake Villa, both of Ill.; David R. Mees, St. Louis, Mo.; Mary K. Joseph; Terry A. Pry, both of Libertyville, Ill.; C. Brent Putman, Round Lake Beach, Ill.; Daniel D. Subotich, Morton Grove, Ill.

[73] Assignee: Abbott Laboratories, Abbott Park, Ill.

[21] Appl. No.: 657,578

[22] Filed: Jun. 7, 1996

[51] Int. Cl.⁶ .................. G01N 33/543; G01N 33/544; G01N 33/546; C12Q 1/00
[52] U.S. Cl. .............. 436/518; 436/523; 436/528; 436/529; 436/530; 436/531; 436/533; 436/534; 436/823; 436/548; 436/810; 435/4; 435/7.9; 435/962; 435/963
[58] Field of Search ................... 435/4, 7.9, 962, 435/963; 436/518, 523, 528–531, 533–534, 823, 548, 810

[56] References Cited

U.S. PATENT DOCUMENTS 5,252,459  10/1993  Tarcha et al. ................. 435/6

OTHER PUBLICATIONS

P. J. Tarcha, et al., "Synthesis, Analysis, and Immunodiagnostic Applications of Polypyrrole Latex and Its Derivatives", American Chemial Society, vol. 492, 1992, pp. 347–367.

J. F. Pritchard, et al., "Determination of Vicinal Hydroxyl Groups in Poly(Vinyl Alcohol) (PVA)", Talanta, vol. 23, 1975, pp.237–239.

*Primary Examiner*—Lila Feisee
*Assistant Examiner*—Sheela J. Huff
*Attorney, Agent, or Firm*—David L. Weinstein

[57] ABSTRACT

A method for increasing the binding activity of specific binding members bound to a solid phase material, e.g., a particle, that has been sterically stabilized. This increase in binding activity is brought about by degrading a steric stabilizer on the surface of the solid phase material. The method involves both immobilizing a specific binding member on the surface of a solid phase material and degrading a steric stabilizer on the surface of that solid phase material. In the preferred embodiment, the method involves the immobilization of a specific binding member on the surface of the sterically stabilized solid phase material, with subsequent degradation of the steric stabilizer.

18 Claims, 2 Drawing Sheets

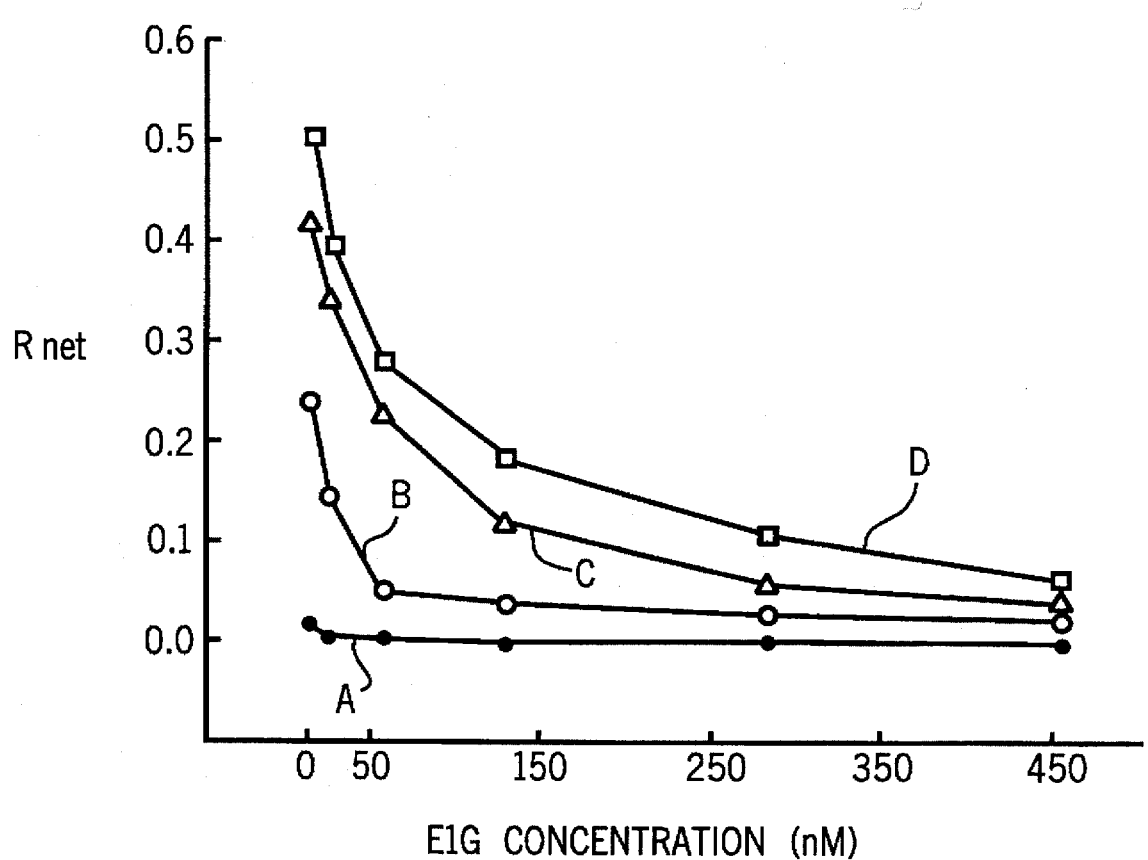

5,681,754

METHOD FOR IMPROVING THE PERFORMANCE OF AN IMMUNOREAGENT IN AN IMMUNOASSAY

BACKGROUND OF THE INVENTION

1. Field of the Invention

This invention relates to a method for improving the performance of an immobilized specific binding member in an immunoassay, more particularly, an immunoassay that utilizes a specific binding member immobilized on a solid phase material.

2. Discussion of the Art

Various analytical procedures can be used in diagnostic assays to determine the presence and/or amount of substances of interest or clinical significance in test samples, such as body fluids. These interesting or clinically significant substances are commonly referred to as analytes. Diagnostic assays have become an indispensable means for detecting analytes in test samples by using the reaction between the analyte and a specific binding member, as typified by the immunoreaction between an antigen and the antibody to that antigen.

In detecting immunoreactions, use has been made of tags or labels composed of a traceable substance that is attached to a specific binding member, such as an antibody, which, in turn, binds to the analyte to form an antibody/analyte complex. The detection of the labeled antibody/analyte complex, or of the labeled antibody that remains unbound, indicates the presence or amount of the analyte in the test sample.

Assay techniques using metallic sol particles as labels have been developed. In these techniques, a metal (e.g., gold, silver, platinum), a metal compound, or a nonmetallic substance, such as selenium, is used to form an aqueous dispersion of particles. The specific binding member to be labeled is coated onto the sol particles by adsorption. The sol particles can produce a signal that is both visually detectable and measurable by an instrument; however, despite their utility, the surfaces of these sol particles, such as gold or selenium, do not readily accept the covalent attachment of specific binding members. Thus, care must be taken so that the adsorbed specific binding members are not removed from the sol particles through the combination of displacement by other proteins or surface active agents and the shear forces that accompany washing.

Particulate labels in immunoassay reagents have also been formed from polymerized dyes. Dye molecules, i.e., chromogenic monomers, are polymerized to form a colored polymeric particle. The dye particles can then be linked to a specific binding member for use in an assay. Examples of such dyes include Congo red, Trypan blue, and Lissamine blue.

Polypyrrole particles, often referred to as polypyrrole latex, have been used as a colored indicator for immunoassays. Polypyrrole latex offers several advantages for the formulation of immunoreagents. The latex is intrinsically black, having a high absorption of light over the full visible spectrum. This property makes the particles useful in detection reagents, either for visual- or instrument-based detection. U.S. Pat. No. 5,252,459 discloses the use of polypyrrole latex in diagnostic applications.

The use of polypyrrole in the form of colloidal particles as an immunodiagnostic reagent has been limited by low apparent activity in various assay formats, and by a tendency for assay performance to change over time. The low activity results from interference of specific binding members by steric stabilizers, which were used during the formation of the polypyrrole latex. The cause of change in assay performance is a result of the change in the steric stabilizers over time. Steric stabilizers cannot be easily removed from the base latex during purification, and hence are present on the surface of the particle in the final immunoreagent.

Immunodiagnostic reagents are prepared by the adsorption of a specific binding member, such as an antibody, to a colloidal particle in a process referred to as "coating" the particle. There have been two primary disadvantages to the use of colloidal particles of polypyrrole as a component of an immunodiagnostic reagent. Colloidal particles that are coated immediately after they are synthesized and purified have been found to exhibit limited specific binding activity in immunoassays that are dependent upon agglutination or solid phase capture of the colloidal particles. Upon prolonged storage of the uncoated colloidal particles, newly prepared immunoreagents have been observed to show improved performance. The time that is needed to put the particles in proper condition for use in an immunoassay is often long (e.g., weeks or months) and varies among preparations of the particles. It was observed that this "aging" was accelerated at elevated temperatures. For example, conjugates comprising antibody coated upon colloidal particles of polypyrrole that had been mixed at 37° C. for 72 hours were found to demonstrate significantly enhanced specific binding activity. Extended periods of thermal treatment of both the coated and uncoated latex have been used to enhance assay performance; however, aging continues subsequent to thermal treatment.

Although thermal aging improved the specific binding activity of specific binding members immobilized on colloidal particles of polypyrrole, the thermal "aging" of colloidal particles of polypyrrole introduced an additional limitation. Immunoreagents prepared from different lots of "aged" polypyrrole demonstrated different levels of specific binding activity. Furthermore, preparations of uncoated, aged polypyrrole continued to change as the duration of storage increased. In some cases, extended aging, either through prolonged thermal treatment or prolonged storage, led to aggregation of the colloidal particles, rendering them useless. The variations of specific binding activity resulting from storage and variation from lot-to-lot made it difficult to provide reproducible immunoreagents made from particles of polypyrrole. As stated previously, the time needed to put colloidal particles of polypyrrole in proper condition for use in an immunoassay was often long, ranging from weeks to months, and the particles varied from batch-to-batch.

It would be desirable to develop a method for controlling the preparation of colloidal immunoreagents comprising colloidal particles in order to ensure reproducible results. It would be desirable to reduce "aging" following synthesis. Even with accelerated aging by thermal treatment, colloidal particles continue to change over time, and the coating process often results in aggregation of the colloidal particles.

SUMMARY OF THE INVENTION

This invention provides a method for increasing the binding activity of specific binding members bound to a solid phase material, e.g., a particle, that has been sterically stabilized. This increase in binding activity is brought about by degrading a steric stabilizer on the surface of the solid phase material. In general, the method involves both immobilizing a specific binding member on the surface of a solid phase material having a steric stabilizer thereon and degrading the steric stabilizer. In the preferred embodiment, the method involves the immobilization of a specific binding member on the surface of the sterically stabilized solid phase material, with subsequent degradation of the steric stabilizer. Alternatively, but less preferably, the steric stabilizer may be degraded prior to the immobilization of the specific binding member on the surface of the solid phase material. In the latter case, precautions must be taken to insure colloidal stability of the solid phase material prior to the immobilization. Such precautions include maintaining low ionic strength, control of pH, and the use of surfactants. The method of the preferred embodiment provides for colloidal stability during the immobilization step, because specific binding members, such as, for example, proteins, are known to be effective stabilizers of colloids. Both embodiments provide for enhanced binding activity of the immunoreagent upon completion of the method. The specific activity of the immunoreagent can be enhanced by controlling the conditions of degradation and the concentrations of solid phase materials and specific binding members used.

In the present invention, the steric stabilizer used to prepare the solid phase material is degraded during the process of preparing an immunoreagent comprising a specific binding member. The degradation of the steric stabilizer results in increasing the accessibility of the bound specific binding member to the complementary member of its specific binding pair. This change in accessibility is reflected in a measured enhancement of the specific activity of the immunoreagent.

In the specific case of polypyrrole, the method preferably involves storage of initially prepared colloidal particles of polypyrrole, typically at reduced temperature, preferably under nitrogen, and subsequent degradation of the steric stabilizer by means of oxidation, preferably by means of periodate oxidation. In the specific case of polypyrrole, the method of the present invention, in effect, both halts the aging of the colloidal particles and selectively oxidizes the steric stabilizer, typically poly(vinyl alcohol), used in the preparation of the colloidal particles.

BRIEF DESCRIPTION OF THE DRAWINGS

FIG. 3 is a graph illustrating the effect of controlled oxygen exposure on the specific activity of polypyrrole immunoreagents for an E1G immunoassay.

DETAILED DESCRIPTION

Figure 1:
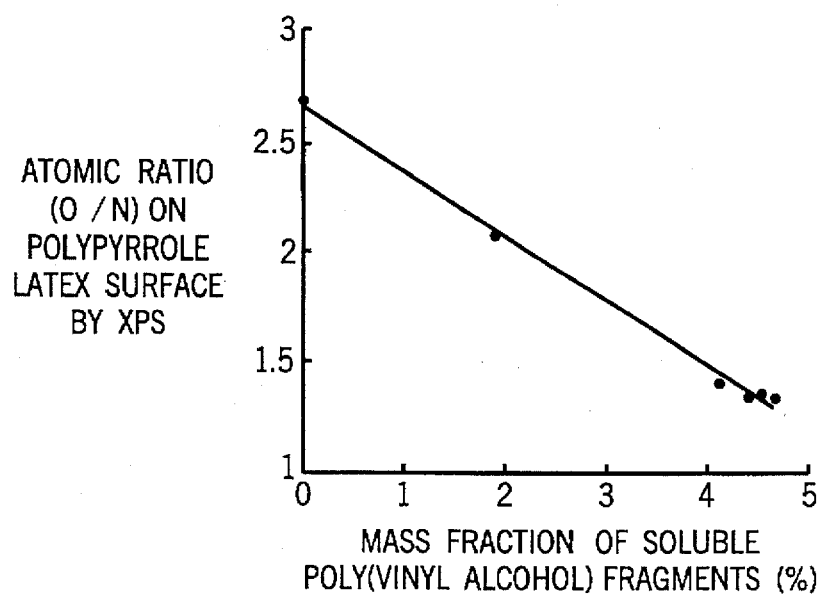
FIG. 1 is a graph comparing the ratio of atomic percent oxygen to nitrogen on the surface of colloidal particles as a function of the calculated percentage of mass lost resulting from reaction with periodate. The atomic percentages were obtained by X-ray photoelectron spectroscopy (XPS).

The following terms and expressions may be useful in understanding the present invention.

"Specific binding member," as used herein, means a member of a specific binding pair; i.e., two different molecules where one of the molecules through chemical or physical means specifically binds to the second molecule. In addition to antigen and antibody-specific bindings pairs, other specific binding pairs include biotin and avidin, carbohydrates and lectins, complementary nucleotide sequences (including probe and capture nucleic acid sequences used in DNA hybridization assays to detect a target nucleic acid sequence), complementary peptide sequences, effector and receptor molecules, enzyme cofactors and enzymes, enzyme inhibitors and enzymes, and the like. Furthermore, specific binding pairs can include members that are analogs of the original specific binding member. For example, a derivative or fragment of the analyte (i.e., an analyte-analog) can be used so long as it has at least one epitope in common with the analyte. Immunoreactive specific binding members include antigens, haptens, antibodies, and complexes thereof, including those formed by recombinant DNA methods or peptide synthesis.

"Analyte," as used herein, means the substance to be detected in a test sample. An analyte can be any substances for which there exists a naturally occurring specific binding member (e.g., an antibody) or for which a specific binding member can be prepared, and the analyte can bind to one or more specific binding members in an assay. "Analyte" also includes any antigenic substances, haptens, antibodies, and combinations thereof. The analyte can include a protein, a peptide, an amino acid, a hormone, asteroid, a vitamin, a drug, including those administered for therapeutic purposes as well as those administered for illicit purposes, a bacterium, a virus, and metabolites of or antibodies to any of the above substances.

"Indicator reagent," as used herein, means a detectable label directly or indirectly attached to a specific binding member.

"Capture reagent," as used herein, means a specific binding member capable of binding the analyte or indicator reagent and which can be directly or indirectly attached to a substantially solid material to form a solid phase capture reagent complex. The solid phase capture reagent complex can be used to separate the bound and unbound components of the assay.

"Ancillary specific binding member," as used herein, means a specific binding member used in addition to the specific binding members of the capture reagent and the indicator reagent, which becomes a part of the final binding complex. One or more ancillary specific binding members can be used in an assay. For example, an ancillary specific binding member can be used in an assay where the indicator reagent is capable of binding the ancillary specific binding member, which, in turn, is capable of binding the analyte.

"Latex", as used herein, means a colloidal dispersion of polymeric particles, where water is typically the continuous phase or medium. The particles typically range in size from about 20 to about 1000 nm.

"Colloid", as used herein", means a dispersion of particles, which particles typically have a size ranging from about 10 to about 1000 nm. Colloidal material can be organic or inorganic, and the continuous phase can be aqueous, organic, or gaseous.

"Particle", as used herein, means a colloid or a latex.

"Steric stabilizer", as used herein, means a polymeric material that is attached to the surface of a colloidal particle and that serves to keep colloidal particles from agglomerating. The steric stabilizer is always solvated by the continuous phase into which a surface is immersed or a colloidal dispersion is dispersed.

In one aspect, this invention provides a method for increasing the binding activity of specific binding members bound to a solid phase material, e.g., a particle, that has been sterically stabilized. This increase in binding activity is brought about by degrading a steric stabilizer on the surface of the solid phase material.

In general, the method involves both immobilizing a specific binding member on the surface of a solid phase material and degrading a steric stabilizer on the surface of that solid phase material. In the preferred embodiment, the method involves the immobilization of a specific binding member on the surface of the sterically stabilized solid phase material, with subsequent degradation of the steric stabilizer. Alternatively, but less preferably, the steric stabilizer may be degraded prior to the immobilization of the specific binding member on the surface of the solid phase material.

The polymerization of polypyrrole latex typically involves the use of a water soluble steric stabilizer. The preferred steric stabilizer is poly(vinyl alcohol). The steric stabilizer maintains the colloidal stability of the polypyrrole latex during and after synthesis. Synthesis of colloidal particles is described in U. S. Pat. No. 5,252,459, incorporated herein by reference. Colloidal stability means that the particles of polypyrrole resist aggregation. The steric stabilizer has been found to interfere with the ability of a specific binding member immobilized on the surface of a colloidal particle to bind to a complementary specific binding member immobilized on the surface of a second solid phase. This invention provides for the controlled removal of a portion of the steric stabilizer, resulting in significant enhancement of the specific binding ability of the specific binding member immobilized on the surface of the colloidal particle of polypyrrole.

Controlled removal of the portion of the steric stabilizer can be carried out by means of a chemical agent, preferably an oxidizing agent, or a biological agent, preferably an enzyme. Oxidizing agents suitable for removal of the appropriate portion of the steric stabilizer preferably cleave at an appropriate cleavage site.

Degradable species of steric stabilizers include entities containing ester linkages, amide linkages, vicinal diol linkages, disulfide linkages, and carbohydrate linkages. In the preferred method of this invention, colloidal particles of polypyrrole coated with antibody and stabilized by poly (vinyl alcohol) are treated with periodic acid or lead tetra acetate. The functional sites of interest in poly(vinyl alcohol) are the vicinal diol sites. These sites originate from the relatively infrequent head-to-head addition during polymerization of the precursor monomer, vinyl acetate. The acetate groups are subsequently hydrolyzed to produce the poly (vinyl alcohol).

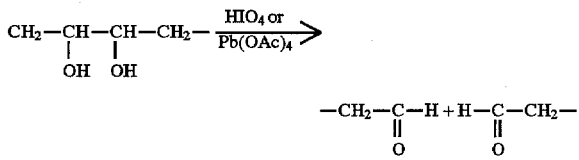

Alternatively, other oxidizing agents may be used, including activated manganese dioxide, thallium III salts, permanganate, and dichromate. The lead tetraacetate would require an organic co-solvent with the aqueous solvent. Permanganate and dichromate may be too harsh for use in conjunction with antibodies. Molecular oxygen can cause degradation of polyvinyl alcohol in the presence of polypyrrole latex, apparently due to a catalytic effect of the polypyrrole surface. The generation of low molecular weight poly(vinyl alcohol) in this situation can be confirmed by size exclusion chromatography. In contrast, reflux of an aqueous solution of poly(vinyl alcohol), in the absence of polypyrrole, using a flask equipped with an oxygen ebulliator tube, caused no apparent degradation.

The cleavage at the vicinal diol sites results in the lowering of the molecular weight of the polyvinyl alcohol and subsequent release of a portion of the stabilizer, with concomitant increase in specific binding ability. The extent of stabilizer cleavage is controlled by the conditions of concentration of oxidizing agent, temperature, time, and pH. In the embodiment wherein polypyrrole stabilized by poly (vinyl alcohol) is the solid phase, it is preferred that the concentration of oxidizing agent, i.e., periodate, range from about 5 mM to about 100 mM. It is preferred that the temperature range from about 4° C. to about 37° C. It is preferred that the duration of oxidation range from about 15 minutes to about 24 hours. It is preferred that the oxidation take place under acidic conditions, more preferably with the pH ranging from about 5 to about 7. The oxidative treatment of the latex may be performed either prior to, or subsequent to, the coating with the specific binding member. The specific binding member may be adsorbed onto, or covalently bound to, the colloidal particles.

The molecular weight of the steric stabilizer is not critical to the invention. Of course, the steric stabilizer must contain at least one site for cleavage. Other stabilizers that are capable of being degraded may be used. An example of an alternative stabilizer are carbohydrate polymers, which can be degraded with appropriate glycohydrolytic enzymes. The method of this invention may be applied to all colloids that possess an associated polymeric layer, with appropriate modifications to the method. Such colloids include metal sols, colloidal metal oxides, ceramics, non-metal sols, e.g., selenium, sulfur, carbon, silicon. Composite colloids can also be used. Examples of composite colloids are particles comprising both polypyrrole and selenium in a single entity and a colloid comprising both polypyrrole and silica in a single entity.

Colloids suitable for use in the present invention can be made by polymerizing a nonchromophoric monomer; nonchromophoric monomer, as used herein, refers to an organic monomer that is neither a pigment nor a dye and that has color or absorbance characteristics that make the unpolymerized substance unsuitable for use as a detectable label. A method for preparing these colloids is described in U.S. Pat. No. 5,252,459, previously incorporated herein by reference. Other polymeric latex particles suitable for use in this invention, include, but are not limited to, the particles in the classes described in U.S. Pat. No. 5,252,459, at column 10, line 24 through column 11, line 25 thereof.

The present invention provides a controllable method for preparing immunoreagents comprising colloidal particles that exhibit minimal variation from lot-to-lot. Storage of uncoated colloidal particles at a low temperature (e. g., 4° to 8° C.) under an inert atmosphere (e.g., nitrogen), protected from light, maintains the properties of the surface of the colloidal particles in such a manner that they are comparable to recently synthesized, "non-aged" colloidal particles. Colloidal particles stored under these conditions, and subsequently treated by the degradation step described herein, provide immunoreagents that show little variation from lot-to-lot. The performance is insensitive to the specific lot of colloidal particles, or the duration of storage before coating of the specific binding member. Previous methods for preparing colloidal particles of polypyrrole coated with specific binding members have frequently resulted in aggregated preparations, which require ultrasonication, or other mechanical means of redispersion. Immunoreagents prepared by the method of this invention retain their colloidal stability, and require little or no redispersion.

The following examples are illustrative of the invention and are not to be interpreted as limiting the scope of the invention, as defined in the claims.

EXAMPLE 1

Treatment Of Poly(Vinyl Alcohol) Solutions With Periodate And Subsequent Molecular Weight Analysis By High-Performance Size-Exclusion Chromatography (HPSEC)

This example illustrates the degradation of poly(vinyl alcohol), in solution, by periodate oxidation.

Analysis of the molecular weight averages (weight average, $M_w$; and number average, $M_N$) was performed as described in W. W. Yau, J. J. Kirkland, and D. D. Bly, Modern Size-Exclusion Liquid Chromatography, John Wiley & Sons (1979). Molecular weight analysis of the undegraded high molecular weight poly(vinyl alcohol) required a somewhat different experimental procedure than did the analysis of the fragments.

Analysis of Undegraded Poly(vinyl alcohol)

The poly(vinyl alcohol) used as the steric stabilizer in the preparation of colloidal particles of polypyrrole was sold under the trademark "ELVANOL HV" (E. I. Du Pont de Nemours). The vendor specification for this polymer indicated 99.0 to 99.8% hydrolysis (mole percent hydrolysis of acetate groups). The poly(vinyl alcohol) was analyzed for molecular weight distribution by HPSEC. Three HPSEC columns were used in series: GMPW (Tosohaas), G3000PW (Tosohaas), and SEC-S2000 (Phenomenex). Water was used as the mobile phase at a flow rate of 1.0 ml/min and detection was carried out by evaporative light scattering (ELSD MKIII, Alltech Associates). A molecular weight calibration curve was established using poly(ethylene oxide) standards (Phenomenex) at concentrations of 0.05 and 0.5% (w/v) with a range of 10,000 to 1,390,000 g/mole. The sample of poly(vinyl alcohol) was dissolved in water at a concentration of 0.08% (w/v) and 0.1 ml was injected for analysis. The calculated averages for "ELVANOL HV" were $M_w$, =135,600 g/mole and $M_N$=71,400 g/mole. $M_W$ means weight average molecular weight. $M_N$ means number average molecular weight.

Analysis of Degradation Fragments

For the periodate treatment of poly(vinyl alcohol), aqueous solutions at concentrations ranging from 0.03% to 1.0% were prepared (w/vl). Periodic acid (0.5M) was prepared in water and the pH was adjusted to 6.5 with triethanolamine. An aliquot of periodate solution (1.1 ml) was added to poly(vinyl alcohol) (10 ml), providing a final concentration of 50 mM periodate, and the reaction was allowed to proceed for 15 hours at a temperature of at 8° C, protected from light. The products of the reaction were analyzed by HPSEC. Three SEC-S2000 columns (Phenomenex) were used in series, with a mobile phase of 0.1M sodium nitrate at a flow rate of 1.0 ml/min, and detection was carried out by differential refractive index. A calibration curve was established using poly(vinyl alcohol), dextrans, and small carbohydrates for a molecular weight range of 200 to 10,500 g/mole. Sample injections of 0.05 ml were made for analysis. Under these conditions, molecules with molecular weight exceeding 26,000 g/mole are excluded. The calculated averages for the oxidized product were $M_w$=5,800 g/mole and $M_N$=5,100 g/mole. Under these conditions, there was no evidence of polymer with $M_W$ exceeding 12,000 g/mole.

EXAMPLE 2

Treatment Of Polyvinyl Alcohol-Stabilized Latex With Periodate And Subsequent Analysis Of The Latex Surface By X-Ray Photoelectron Spectroscopy (XPS) And Solution Fragments By HPSEC This example illustrates the degradation of the steric stabilizer poly(vinyl alcohol) on polypyrrole latex by periodate oxidation.

Suspensions of polypyrrole (1% w/v) were treated with the periodate-triethanolamine solution as described in Example 1 (Analysis of Degradation Fragments). The final concentration of periodate was varied from 0 mM to 50 mM to determine its effect on the released material. Following the 15 hour oxidation period, the suspension was centrifuged at 40,000 rpm for 30 minutes. The supernatant was removed and centrifuged for an additional 2 hours at 40,000 rpm. The final supernatant was filtered through cellulose acetate membrane (0.2 mm pore size) and analyzed by HPSEC as previously described. Estimation of fragment mass was made by comparison of the peak intensities with a standard curve prepared by a dilution series for periodate treated poly(vinyl alcohol). The resulting estimate of mass was evaluated as mass fraction, based on the initial mass of polypyrrole latex. There was no evidence in any of the samples for fragments with $M_w$ exceeding 12,000 g/mole.

| HPSEC Analysis of Soluble Polymer from Periodate Treated Polypyrrole | | | |
|---|---|---|---|
| Concentration of periodate (mM) | $M_W$ (g/mole) | $M_N$ (g/mole) | Mass fraction of poly(vinyl alcohol) fragment |
| 0 | None | None | 0 |
| 10 | 6900 | 5900 | 0.019 |
| 20 | 5500 | 4800 | 0.041 |
| 30 | 5000 | 4500 | 0.044 |
| 40 | 5100 | 4600 | 0.045 |
| 50 | 4000 | 3500 | 0.047 |

The latex collected from each of the above preparations was further cleaned by three repeated cycles of resuspension in deionized water, followed by centrifugation and a final resuspension in 10 ml of deionized water. The latex preparations were analyzed for surface elemental composition by X-ray Photoelectron Spectroscopy (XPS) for oxygen (O), nitrogen (N), and carbon (C). The elemental composition and atomic percent ratio of oxygen to nitrogen (O/N) was used to monitor the loss of steric stabilizer.

| XPS Surface Elemental Analysis of Periodate Treated Polylpyrrole | | | | |
|---|---|---|---|---|
| Concentration of periodate (mM) | O (%) | N (%) | C (%) | O/N |
| 0 | 22.8 | 8.5 | 66.6 | 2.68 |
| 10 | 20.6 | 9.9 | 68.3 | 2.08 |
| 20 | 17.8 | 12.5 | 68.6 | 1.42 |
| 30 | 17.3 | 12.7 | 69.1 | 1.36 |
| 40 | 17.3 | 12.7 | 68.9 | 1.36 |
| 50 | 16.7 | 12.5 | 69.8 | 1.34 |

The HPSEC and XPS analyses are complementary. The analyses provide quantitative data for the soluble and insoluble reaction products, respectively. A comparison of the ratio of O/N (XPS) on the surface of the colloidal particles as a function of the calculated % mass loss (HPSEC) is shown in FIG. 1. Percent mass loss is equal to mass fraction times 100%. The linear regression correlation coefficient for the comparison ($R^2$) is 0.997.

Example 3

Periodate Oxidation Of Poly(Vinyl Alcohol)- Stabilized Polypyrrole Latex Coated With Anti- Estradione-1-Glucuronide (E1 G) Antibody This example illustrates preparation of a colloidal conjugate comprising polypyrrole and anti-E1G antibody, and the subsequent degradation of the poly(vinyl alcohol) steric stabilizer by periodate oxidation.

All reagents used in the preparation were brought to a temperature of 45° C. in a circulating water bath prior to the coating process. Borate buffer (0.25 ml, 100 mM sodium borate, pH 10) was placed into a vial, followed by additions of 1.0% (w/v) "BRIJ 35" polyoxyethylene ether (0.50 ml in deionized water), deionized water (1.51 ml), and polypyrrole (2.50 ml, 2.0% solids in deionized water). Murine monoclonal antibody (about 0.25 ml, 11.4 mg/ml) specific for estradione-1-glucuronide (E1G), was added to the polypyrrole latex suspension with stirring. The mixture was incubated at a temperature of 45° C for two hours. Then an overcoat solution was added (1.70 ml, 0.25M BIS-TRIS, 4.0% (w/v) bovine serum albumin, 0.1% (w/v) "BRIJ 35" polyoxyethylene ether, pH 7.0). The mixture was incubated, with mixing, at a temperature of 45° C. for an additional 10 minutes The coated latex suspension was then maintained at a temperature of 4 to 8° C. for one hour. As the suspension was stirred continuously, periodate solution (0.75 ml, 0.3M periodic acid neutralized to pH 6–7 with triethanolamine) was added to the suspension. The suspension was mixed at a temperature of 4° to 8° C., protected from ambient light, for 15 to 18 hours. Following oxidation, the coated latex was cleaned by hollow-fiber tangential filtration, using a suitable exchange buffer (25 mM MOPS, 0.5% bovine serum albumin, 0.1% "BRIJ 35" polyoxyethylene ether, adjusted to pH 7.2 with ethanolamine). The suspension was stored at a temperature of 4° to 8° C. until used.

EXAMPLE 4

Quantitative Immunoassay Standard Curve For E1G Comparing Untreated And Periodate Treated Immunoreagents This example illustrates the use of a polypyrrole colloidal conjugate in an immunoassay.

A competitive assay format was used to develop an immunoassay to detect the presence and amount of E1G.

The chromatographic strip used in the assay was substantially similar to the chromatographic strip described in U.S. Pat. No. 5,252,459, Examples 1 and 2. At one end of a chromatographic strip was deposited 0.01% latex (w/v) (0.025 ml ), treated as described in Example 3.

Figure 2:
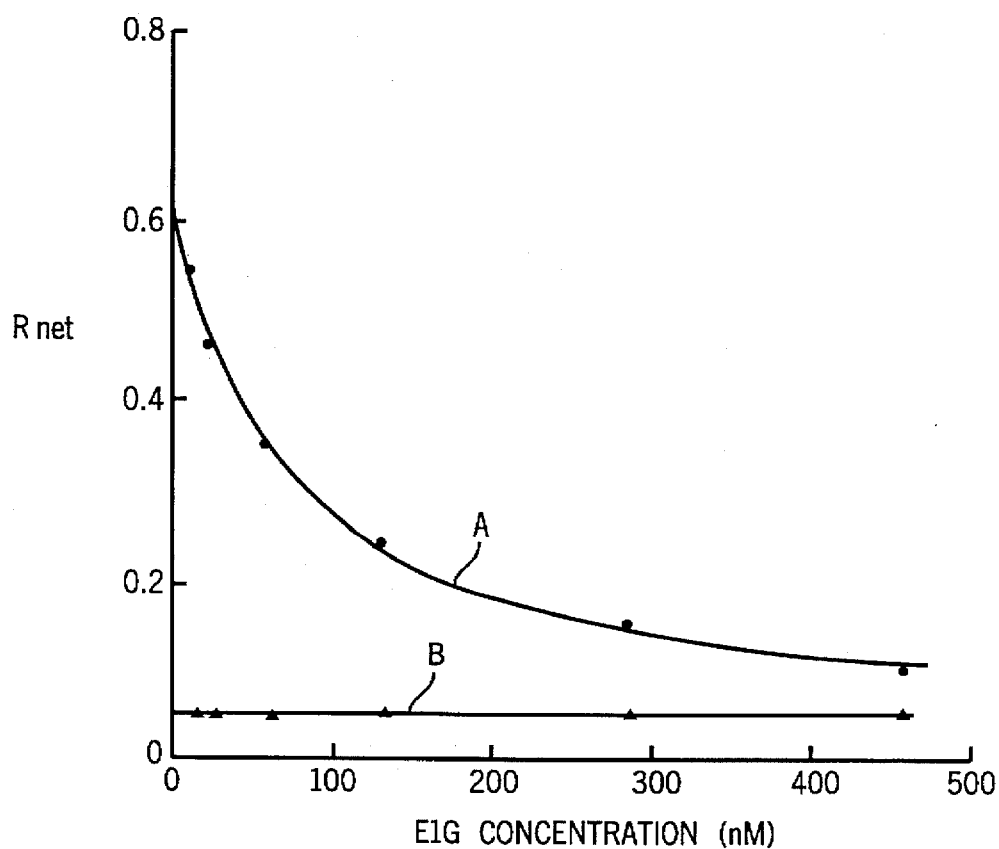
FIG. 2 is a graph illustrating the effect of periodate oxygen on the specific activity of polypyrrole immunoreagents for an estradione-1-glucuronide (E1G) immunoassay.

Midway along the strip was located a capture zone consisting of a conjugate of bovine IgG and E1G. The capture zone was deposited as a horizontal bar having the dimensions 0.5 mm by 4.0 mm. The latex disposed at the end of the strip was mixed with a liquid sample to be tested, and the resulting mixture was drawn up the strip by absorption and capillary action. In this assay format, if E1G is present in the sample, it binds to the antibody on the polypyrrole latex and diminishes the amount of latex that binds to the conjugate immobilized in the capture zone. This results in a lighter-colored capture region. The concentration of E1G in the sample is inversely related to the amount of latex bound to the conjugate immobilized in the capture zone. Instrumentation that quantitates the amount of bound latex, such as scanning densitometry, may be used to determine the concentration of E1G in the sample. FIG. 2 shows the data from two standard curves, generated using a dilution series of E1G. One curve, Curve A, was generated using unoxidized polypyrrole latex immunoreagent, and the other curve, Curve B, was generated using polypyrrole latex treated by the method of this invention. The signal in this example was obtained by scanning densitometry, and was reported as the net difference in measured background reflectance and the capture zone reflectance (Rnet). The greater the value of Rnet, the greater the amount of captured latex. The data for this comparison is also presented in the table below.

| Effect of Periodate Oxidation on the Specific Activity of Polypyrrole Immunoreagents for E1G | | |
|---|---|---|
| Concentration of E1G (nM) | Net Reflectance for non-oxidized polypyrrole reagent | Net Reflectance for oxidized polypyrrole reagent |
| 11 | 0.0535 | 0.5485 |
| 23 | 0.0525 | 0.4695 |
| 57 | 0.0480 | 0.3620 |
| 129 | 0.0535 | 0.2505 |
| 283 | 0.0505 | 0.1545 |
| 455 | 0.0505 | 0.0950 |

The data demonstrates the enhancement of assay results by the periodate oxidation of the steric stabilizer.

EXAMPLE 5

This example is a prophetic example illustrating the use of a steric stabilizer other than poly(vinyl alcohol).

A protein (2.0 g, "SUPRO-TEIN V" (a potassium/triethanolamine salt of collagen protein condensed with coconut fatty acid and partially complexed with sorbitol)) is added to distilled water (100 ml). Then ferric chloride hexahydrate (17.6 g) is dissolved in distilled water (100 ml), filtered, and combined with the solution containing "SUPRO-TEIN V" protein. With stirring, distilled pyrrole (2.0 ml) is added all at once, and particles of polypyrrole form. The reaction is allowed to proceed for four hours. The polypyrrole suspension is cleaned by cross-flow filtration (sometimes referred to as diafiltration) until the conductivity of the effluent is less than 500 times that of distilled water. The suspension is then exchanged into 0.01M $CaCl_2$ (0.05M MOPS buffer, pH 7.8). The $CaCl_2$ solution may contain 1% Brij 35, a low molecular weight surfactant, to aid in colloidal stability. Then pronase (200–100 micrograms) is dissolved in $CaCl_2$ solution (5 ml), and the resulting solution is added to the polypyrrole suspension to digest the protein. The reaction is conducted at a temperature of 37° C. for 120 hours. Then the suspension is repurified by cross-flow filtration. The suspension can be used in formulation of immunoreagents by coating the particles with antibody or other specific binding member.

EXAMPLE 6

This example is a prophetic example illustrating the use of a steric stabilizer other than poly(vinyl alcohol).

Dextran 75 (2.0 g, avg. mol. wt: 75,000) is added to distilled water (100 ml). Then ferric chloride hexahydrate (17.6 g) is dissolved in distilled water (100 ml), filtered, and combined with the solution of dextran. With stirring, distilled pyrrole (2.0 ml) is added all at once and particles of polypyrrole form. The reaction is allowed to proceed for four hours. The polypyrrole suspension is cleaned by diafiltration until the conductivity of the effluent is less than 500 times that of distilled water. The suspension is exchanged into 0.1M potassium phosphate (pH 6.0) and coated with the antibody of choice for making the immunoreagent. Then dextranase (500 micrograms), having an activity of 200 units, where one unit is defined as producing 1.0 micromole of isomaltose per minute, is dissolved in phosphate buffer (5 ml, pH 6.0). The dextranase solution is added to the suspension. The suspension is maintained at a temperature of 37° C. for 30 minutes, whereupon the dextran is degraded. The immunoreagent suspension can be further purified by centrifugation and washing with phosphate buffer.

EXAMPLE 7

This example compares quantitative immunoassay standard curve for E1G for polypyrrole aged with and without oxygen present.

Polypyrrole was synthesized, and reaction by-products were subsequently removed by diafiltration. The freshly prepared polypyrrole, suspended in distilled water (<300 µmho conductivity), was stored in gas-tight glass bottles having crimp-top rubber septa seals. Nitrogen was bubbled through the polypyrrole by means of feed and vent hypodermic needles to remove the dissolved and atmospheric oxygen present. Three gas-tight bottles filled with polypyrrole were purged by means of similar procedures with pure oxygen, so that headspace oxygen molecules remaining inside the bottles amounted to approximately 1.5 equivalents relative to pyrrole repeat units present. The final conditions were as follows: 10.5 ml of 2.0 % (w/v) polypyrrole, and 118 ml of oxygen head at 1 atmosphere pressure. The polypyrrole under nitrogen was maintained at a temperature of 37° C. for 25 days without mixing. The polypyrrole under oxygen was maintained at a temperature of 37° C. for 7 days under the following conditions: no mixing, agitation by rotating table, and magnetic stir-bar mixing. Mixing provided increased exposure to the headspace oxygen during thermal treatment. All of the polypyrrole preparations were evaluated immediately following treatment. The polypyrrole suspensions were coated with anti-E1G antibodies as described in Example 3; however, the coated suspensions were not treated with periodate. Immunoassay curves for the polypyrrole reagents were obtained as described in Example 4. The immunoassay standard curves are shown in FIG. 3. The larger net reflectance (Rnet) obtained with oxygen-aging indicates that more latex was captured. The data for this comparison is also shown in the table below.

Effect of Oxygen Treatment on the Specific Activity of Polypyrrole Immunoreagents for E1G

| Concentration of E1G (nM) | Net Reflectance (polypyrrole under nitrogen; no mixing) | Net Reflectance (polypyrrole under oxygen; no mixing) | Net Reflectance (polypyrrole under oxygen; agitation by rotating table) | Net Reflectance (polypyrrole under oxygen; stir-bar mixing) |
|---|---|---|---|---|
| 11 | 0.018 | 0.242 | 0.417 | 0.504 |
| 23 | 0.007 | 0.148 | 0.343 | 0.396 |
| 57 | 0.003 | 0.053 | 0.228 | 0.282 |
| 129 | 0.000 | 0.039 | 0.121 | 0.184 |
| 283 | 0.000 | 0.028 | 0.060 | 0.107 |
| 455 | 0.000 | 0.022 | 0.041 | 0.064 |

In FIG. 3, Curve A represents the runs where polypyrrole was under nitrogen with no mixing; Curve B represents the runs where polypyrrole was under oxygen with no mixing; Curve C represents the runs where polypyrrole was under oxygen and agitation was carried out by means of the rotating table; Curve D represents the runs where polypyrrole was under oxygen and mixing was carried out by means of the stir-bar.

EXAMPLE 8

Reaction Of Poly(Vinyl Alcohol) Solution With Oxygen In The Presence Of And Absence Of Polypyrrole Latex And The Subsequent Analysis By HPSEC.

This example illustrates the degradation of poly(vinyl alcohol) by oxygen in the presence of polypyrrole latex.

Purified polypyrrole latex (25 ml, 2% solids) was added to a round-bottom bottom flask. Then poly(vinyl alcohol) ("ELVANOL HV", 25 ml, 2 % solids) in distilled water was added to the flask. The flask, which was equipped with a cold water condenser, was heated to 70° C. in a glycerol bath. Pure oxygen was bubbled through the suspension by means of a sparging stone. Samples (1 ml) were removed at intervals and diluted with distilled water (4 ml) and centrifuged at 10,000 rpm for one hour with a "SS-34 SORVAL" rotor (E. I. Du Pont de Nemours) to remove the latex. The clear supernatant was removed for analysis by HPSEC.

Control reactions were conducted in the absence of polypyrrole. Poly(vinyl alcohol) ("ELVANOL HV", 1 g) was dissolved in distilled water (100 ml), with heating, in a round-bottom flask. The flask, which was equipped with a cold water condenser, was heated to 70° C. in a glycerol bath. Pure oxygen was bubbled through the suspension by means of a sparging stone. Samples (2 ml) were removed at intervals for analysis by HPSEC. The pH of the reaction solution was 5.8.

The control reaction previously described was repeated with the addition of 0.5 ml of phosphoric acid. The pH of this reaction mixture was 1.6, which is comparable to the pH of the purified, unbuffered polypyrrole latex suspension.

Analysis of Poly(Vinyl Alcohol) Products

The poly(vinyl alcohol) products were analyzed by HPSEC in the manner described in Example 1. The HPSEC conditions were designed to identify changes in molecular weight below 12,000 g/mole. Samples from the control reactions at pH 5.8 and 1.6 were obtained at intervals over eight hours of oxygen bubbling at 70° C. None of the control samples displayed evidence of fragmentation within the range of HPSEC. The supernatants from the polypyrrole reaction suspension containing poly(vinyl alcohol) were analyzed by HPSEC to calculate average molecular weights.

HPSEC Analysis of Soluble Polymer from Polypyrrole Treated with Oxygen Gas

| Treatment time (hours) | $M_W$ (g/mole) | $M_N$ (g/mole) |
|---|---|---|
| 0 | >12,000 | >12,000 |
| 1.5 | 8,500 | 7,500 |
| 3 | 7,900 | 6,700 |
| 4 | 7,400 | 6,100 |
| 8 | 7,000 | 5,800 |

In all of the control reactions, both Mw and MN were in excess of 12,000 g/mole, regardless of treatment time.

This invention may be used to enhance the binding activity of solid phase immunoreagents that contain adsorbed or covalently linked layers of soluble polymer. The polymer must have functional groups that allow degradation of the polymeric backbone. Treatment of surfaces in the manner described herein can provide reduced steric interference of the immobilized specific binding member, particularly if the immobilized specific binding member is required to interact with a second immobilized binding member. Another advantage provided by this invention is the reduction of the association of the specific binding member with the solvated polymer layer, which may contain domains that exhibit weak affinity for the specific binding member. Specific binding members associated with the polymer layer in this manner may be prone to detachment from the solid phase, when opportunities for stronger interactions are presented, such as, for example, binding to an immobilized ligand for which the specific binding member has specificity.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A process for increasing the binding activity of a specific binding member immobilized on the surface of a solid phase material stabilized with a steric stabilizer comprising the steps of:

(a) immobilizing a specific binding member on the surface of said solid phase material, and (b) degrading said steric stabilizer.

2. The method of claim 1, wherein the step of immobilizing said specific binding member on the surface of said solid phase material occurs prior to the step of degrading said steric stabilizer.

3. The method of claim 1, wherein the step of immobilizing said specific binding member on the surface of said solid phase material occurs subsequent to the step of degrading said steric stabilizer.

4. The method of claim 1, wherein said steric stabilizer is degraded by a chemical agent.

5. The method of claim 4, wherein said chemical agent is an oxidizing agent.

6. The method of claim 5, wherein said oxidizing agent is selected from the group consisting of periodate, lead tetraacetate, activated manganese dioxide, thallium III salts, permanganate, and dichromate.

7. The method of claim 1, wherein said steric stabilizer contains a hydrolyzable linkage.

8. The method of claim 1, wherein said steric stabilizer contains a linkage selected from the group consisting of ester linkages, amide linkages, vicinal diol linkages, disulfide linkages, and carbohydrate linkages.

9. The method of claim 1, wherein said steric stabilizer is degraded by a biological agent.

10. The method of claim 9, wherein said biological agent is an enzyme.

11. The method of claim 1, wherein said solid phase material is a particle.

12. The method of claim 11, wherein said particle is a colloidal particle.

13. The method of claim 1, wherein said solid phase material is a polymer.

14. The method of claim 13, wherein said polymer is prepared by polymerizing nonchromophoric monomeric units.

15. The method of claim 13, wherein said polymer is chromophoric.

16. The method of claim 13, wherein said polymer is polypyrrole.

17. The method of claim 5, wherein said oxidizing agent is oxygen.

18. The method of claim 17, provided that said solid phase material is polypyrrole and said steric stabilizer is poly(vinyl alcohol).

* * * * *